United States Patent [19]

Shields et al.

[11] Patent Number: 4,966,452
[45] Date of Patent: Oct. 30, 1990

[54] CONTACT LENS FOR LASER SURGERY

[75] Inventors: M. Bruce Shields, Durham, N.C.; Phillip J. Erickson, Bellevue, Wash.

[73] Assignees: Ocular Instruments, Inc., Seattle, Wash.; Duke University, Durham, N.C.

[21] Appl. No.: 344,711

[22] Filed: Apr. 27, 1989

[51] Int. Cl.⁵ .................... A61B 1/00; G02C 7/04
[52] U.S. Cl. ..................... 351/219; 351/160 R
[58] Field of Search ..................... 351/219, 160 R

[56] References Cited

U.S. PATENT DOCUMENTS 3,409,349 11/1968 Boyle et al. ..................... 351/219
4,309,085 1/1982 Morrison ........................ 351/219
4,575,205 3/1986 Kappazzo ....................... 351/219

FOREIGN PATENT DOCUMENTS 951219 8/1982 U.S.S.R. ....................... 351/219

Primary Examiner—Rodney B. Bovernick
Attorney, Agent, or Firm—Christensen, O'Connor, Johnson & Kindness

[57] ABSTRACT

A contact lens for use in connection with transscleral cyclophotocoagulation. The lens has a planar entry surface and a frustoconically-shaped exit surface that contacts the sclera surrounding the cornea. The central portion of the lens is opaque to prevent stray laser light from entering the optical portion of the eye during laser application.

7 Claims, 1 Drawing Sheet

U.S. Patent      Oct. 30, 1990      4,966,452
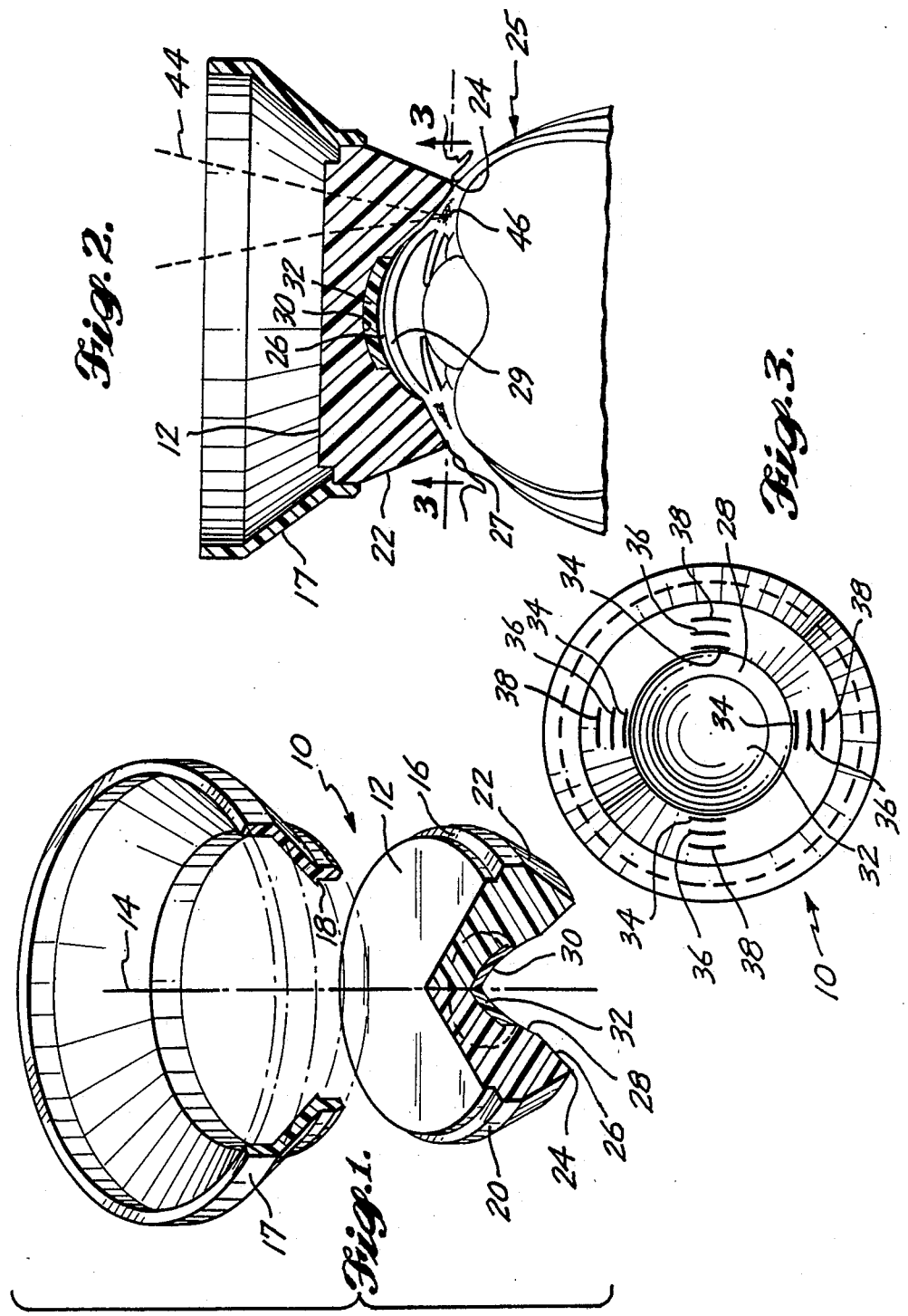

CONTACT LENS FOR LASER SURGERY

FIELD OF THE INVENTION

The present invention relates to optical lenses, and more particularly, to a contact lens for use in conjunction with transscleral cyclophotocoagulation.

BACKGROUND OF THE INVENTION

Glaucoma is a disease of the eye eventually leading to blindness. It is caused by increasing pressure in the eye. The increase in pressure results from the inability of the aqueous humor to escape through the trabecular meshwork. Two conventional methods of treating open-angle glaucoma include administration of drugs to reduce aqueous humor production to increase outflow and laser trabeculoplasty to increase the aqueous humor outflow. Both of these methods have their limitations.

Recently, a new procedure, transsclera cyclophotocoagulation, has been employed to deactivate portions of the ciliary body to reduce aqueous humor production. Transscleral cyclophotocoagulation involves making several laser burns in the ciliary body. Heretofore the cyclophotocoagulation has been practiced by aiming the laser directly at the conjunctiva and sclera adjacent the limbus. Because the laser traverses the sclera close to the cornea it is desirable to protect the optical portions of the eye from stray laser light. It is also desirable and necessary to hold the eyelids away from the sclera where the laser burns are being made, to compress edematous conjunctiva, to blanch congested conjunctival vessels, and to accurately place the laser beams in relation to the limbus.

SUMMARY OF THE INVENTION

The present invention provides a contact lens for use in conjunction with transscleral cyclophotocoagulation that solves the shortcomings associated with the direct application of the laser beam to the sclera. A lens constructed in accordance with the present invention allows some positioning of the eye. The lens eliminates the possibility of stray light entering the optical portion of the eye. The lens also serves to hold the eyelids away from the portion of the sclera where the laser applications are being made. In addition, the lens compresses the conjunctiva of the eye and blanches the blood vessels overlying the sclera, thus minimizing burns to the exterior of the eye. Etched marks on the lens also help in accurate placement of the laser applications.

A lens constructed in accordance with the present invention has an entry surface and a frustoconically-shaped exit surface. The exit surface is angled superiorly toward said entry surface and inwardly relative to the optical axis of the lens. The entry surface is adapted to contact a region on the sclera surrounding the cornea. The lens also has a concave recess located inwardly from the exit surface. The recess has a curvature slightly steeper than the average human cornea. The recess is thus adapted to protect but be spaced from the corneal epithelium when the exit surface contacts the sclera.

BRIEF DESCRIPTION OF THE DRAWINGS

A better understanding of the present invention can be derived by reading the ensuing specification in conjunction with the accompanying drawings wherein:

FIG. 1 is an exploded isometric view in partial cross section of a lens constructed in accordance with the present invention;

FIG. 2 is a cross-sectional view of the lens in contact with an eye; and

FIG. 3 is a view of the inferior surface of the lens along the sight path 3—3 shown in FIG. 2.

DETAILED DESCRIPTION OF THE INVENTION

Referring first to FIGS. 1 and 2, the lens 10 is machined from a cylindrical blank. The lens is composed of polymethylmethacrylate or other suitable optical material that transmits light in the 350 nm to 1500 nm range. The entry surface 12 of the lens is planar and is oriented orthogonally to the optical axis 14 of the lens. An annular shoulder 16 is located about the periphery of the entry surface and has a superior facing edge parallel to the entry surface 12. A lens holder cup 17 having mating shoulder 18 that fits over the exterior cylindrical surface 20 of the lens and abuts the shoulders. The holder cup 17 is secured to the lens with a suitable adhesive or by means of threads. Below the holder cup, the outer surface 22 of the lens has a frustoconical shape tapering inferiorly and inwardly toward the optical axis 14. The outer surface 22 terminates in a lower edge 24, which also forms the outer edge of the exit surface of the lens. The exit surface 26 is also frustoconically shaped. It extends inwardly toward the optical axis 14 and in a superior direction. Preferably, the angle between the exit surface and the optical axis taken along an inferior-superior plane coincident with the optical axis of the lens is on the order of 56°, which corresponds to the angle of the average human sclera where the exit surface of the lens contacts the sclera in use. This angle may be varied if desired to fit a particular patient. The inner diameter of the exit surface is slightly larger than the diameter of the average cornea of the human eye.

A cavity in the form of a spherical recess is formed inside of the exit surface, extends in a superior direction from the inner edge of the exit surface, and is centered on the optical axis of the lens. The radius of curvature of the cavity is slightly less than the radius of the cornea of the human eye. The radius of curvature can range from 6.0 mm to 8.0 mm, but preferably is on the order of 7.45 mm. A second cavity 30 having cylindrical sides with an axis coincident with the optical axis extends in a superior direction from the first cavity 28. The superior surface of the second cavity 30 is also concave having a radius the same as the first cavity 28. The upper cavity is filled with an opaque material (cast in place polymethylmethacrylate) that is secured to the main body of the lens 10. The opaque button 32 prevents light from entering the optical portion of the eye.

Referring now to FIG. 3, locators or aiming marks 34, 36 and 38 are etched onto the bottom surface of the lens. A first set of aiming marks 34 are etched on a first diameter at a location adjacent the outer edges of the first cavity 28. A second set of aiming marks 34 are etched the same distance from the center of the lens along a second diameter orthogonal to the first. These aiming marks are preferably 6 mm from the optical axis, a location corresponding to the location of the limbus when the lens is on the eye. Similarly, sets of aiming marks 34 are etched at a distance of 1 mm outwardly from marks 34 and a third set of marks 38 are etched at yet another 1 mm outwardly from marks 36. These marks assist the ophthalmologist using the lens in properly aiming and positioning each of the laser applications during the transscleral cyclophotocoagulation procedure.

Referring back to FIG. 2, the lens is shown in contact with the human eye 25. The optical axis of the lens is positioned coincident with the optical axis of the eye. The exit surface 26 contacts the sclera 27 adjacent and around the cornea. The cavity 28, having a diameter slightly larger than the diameter of the cornea 42, serves to protect the cornea while being spaced from the cornea to prevent contact with the corneal epithelium. The opaque button 32 in the center of the lens eliminates passage of the light into the eye 40 along the optical axis for a substantial distance on both sides of the optical axis. Thus, stray light from the microscope illumination source as well as stray laser light is kept from entering the optical portion of the eye.

In use, retrobulbar anesthesia is required whenever transscleral cyclophotocoagulation is performed. A viscous bridge, for example, methylcellulose, between the lens and the eye is not essential since the exit surface of the lens compresses the conjunctiva. Nevertheless, it is recommended that a small quantity of such material be placed in the corneal concavity of the lens before applying it to the eye to further protect the corneal epithelium. Because the diameter of the contact portion of the lens is greater than most other contact lenses, the lids must be widely separated when applying the lens to the eye. The retrobulbar anesthesia helps to relax the lids and make it possible to apply the lens in all patients with a normal palpebral fissure.

Although not shown in the drawings, a segment can be removed from one side of the holder cup to facilitate upward rotation of the lens when treating the inferior quadrant, which is otherwise difficult in a patient with a prominent brow. When a lens with the removed segment is employed, it is helpful when first applying the lens to position the truncated portion of the lens to the side, because the flange helps to hold the upper lid and lashes back while treating the superior quadrant.

Beginning at a 12 o'clock position, the exit surface of the lens is pressed firmly against the conjunctiva to compress it and blanch the blood vessels, as shown in FIG. 2. The central-most aiming marks 34 are aligned with the limbus. Laser applications can then be placed either between or beside the outer aimimg marks. As shown in FIG. 2, the laser beam, represented by the converging dashed lines 44, travels along a path nearly parallel to the axis of the lens, and through the lens to the exit surface 26. The laser is focused at a point 46 in the ciliary body.

Since there are four sets of aiming marks, the lens need only be rotated once and only approximately 45° to make all the laser applications. The laser treatments are started in the superior quadrant between the second and third marks, that is, approximately 1.5 mm peripheral to the limbus. As the lateral or nasal quadrant is approached, the applications are placed closer to the second marks or 1 mm peripherally.

In summary, the lens has several features heretofore unavailable. First, the lens maintains separation of the lids, which facilitates access to the perilimbal sclera in all quadrants. The lens compresses the conjunctiva, which maintains a more uniform thickness of tissue that the laser must traverse. Blanching of conjunctival vessels also helps to minimize the absorption of laser energy at that level and reduces the extent of conjunctival burns. The aimimg marks on the exit surface of the lens help to more accurately place the laser applications in relation to the limbus. The opaque button in the center of the corneal portion blocks stray laser light from entering the pupil. Finally, the lens allows a small amount of movement of the anesthetized eye.

The present invention has been disclosed in conjunction with a preferred embodiment. One of ordinary skill will be able to effect various changes, substitutions of equivalents, and other alterations to the embodiments disclosed without departing from the broad concepts disclosed herein. It is therefore intended that the protection afforded by Letters Patent hereon be limited only by the definitions contained in the appended claims and equivalents thereof.

The embodiments of the invention in which an exclusive property or privilege is claimed are defined as follows:

1. A lens for use in ophthalmic surgery comprising:
   a contact lens having an entry surface and a frustoconically-shaped exit surface, said exit surface being angled superiorly toward said entry surface and inwardly relative to the optical axis of said lens, said entry surface being adapted to contact a region on the sclera surrounding the cornea, said lens having a concave recess located inwardly from said exit surface, said recess having a curvature slightly steeper than the average human cornea, said recess being adapted to protect but be spaced from the corneal epithelium when said exit surface contacts said sclera.

2. The lens of claim 1, wherein said lens has an opaque region in the central portion thereof.

3. The lens of claim 2, wherein said opaque region surrounds the optical axis and is immediately superior to said recess.

4. The lens of claim 1, wherein said exit surface further has a plurality of radially-spaced marks along a first diameter and a plurality of radially-spaced marks along another diameter orthogonal to said first.

5. The lens of claim 1, wherein the angle of said exit surface to said axis is approximately 55°.

6. The lens of claim 1, wherein the radius of said recess is in the range of 6.0 mm to 8.0 mm.

7. The lens of claim 6, wherein the radius of said recess is approximately 7.45 mm.

* * * * *